United States Patent [19]

Kruse et al.

[11] Patent Number: 4,935,438

[45] Date of Patent: Jun. 19, 1990

[54] DOPAMINE-β-HYDROXYLASE INHIBITORS

[75] Inventors: Lawrence I. Kruse, Tewin, England; Stephen T. Ross, Berwin; Eliot H. Ohlstein, Plymouth Valley, both of Pa.

[73] Assignee: SmithKline Beckman Corporation, Philadelphia, Pa.

[21] Appl. No.: 138,993

[22] Filed: Dec. 29, 1987

[51] Int. Cl.⁵ ............................................. A61K 31/415
[52] U.S. Cl. ..................................... 514/398; 548/337
[58] Field of Search .......................... 548/337; 514/398

[56] References Cited

U.S. PATENT DOCUMENTS 3,488,423 1/1970 Doebel et al. ................... 548/322 X
3,915,980 10/1975 Gebert et al. ......................... 548/337
4,532,331 7/1985 Frazee et al. .......................... 548/342

FOREIGN PATENT DOCUMENTS 125033 11/1984 European Pat. Off. ............. 548/322
1155580 6/1969 United Kingdom ................ 548/322

OTHER PUBLICATIONS

P. Iversen et al., *Acta Chem. Scand.* 21:279-285 (1967).

Primary Examiner—Richard A. Schwartz
Attorney, Agent, or Firm—Mary E. McCarthy; Stuart R. Suter; Edward T. Lentz

[57] ABSTRACT

Potent dopamine-β-hydroxylase inhibitors having the Formula

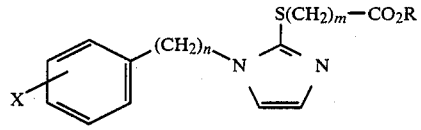

that are useful to inhibit dopamine-β-hydroxylase activity, pharmaceutical compositions including these inhibitors, and methods of using these inhibitors to inhibit dopamine-β-hydroxylase activity in mammals.

6 Claims, No Drawings

DOPAMINE-β-HYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels which as reported by Ehrreich et al., "New Antihypertensive Drugs," Spectrum Publishing, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These generally are divided into two classes, namely, metal chelating agents, which bind copper in the enzyme, and phenethylamine analogues. Rosenberg et al., "Essays in Neurochemistry and Neuropharmacology," Vol. 4, ed. by Youdim et al., John Wiley & Sons, 1980, pp. 179–192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., Heterocycles 14, 755 (1980); Claxton et al., *Eur. J. Pharmacol.* 37, 179 (1976)];

(b) BRL 8242 [See Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See. Johnson et al., *J Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci.* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylalamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoylmethyl)picolinic acid are DBH inhibitors.

Bupicomide, 5(n-butyl)picolinamine, is reported by Ehrreich et al., "New Antihypertensive Drugs", Spectrum Publications, 1976, pg. 409–432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethylimidazole derivatives that inhibit DBH activity and includes pharmaceutical compositions containing these derivatives and methods of using these derivatives to inhibit DBH activity.

Non-specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

Iverson, *Acta Chem. Scand.* 21, 279 (1967) reports compounds having the formula:

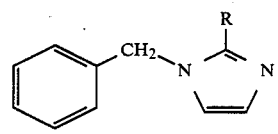

wherein R can be —CO₂H or —CH₂NHC₆H₅, but does not report pharmaceutical uses for the compounds.

In neoprene rubber vulcanization mixtures, 1,3-dihydro 4-phenyl-2H-imidazole 2-thione has been used as a vulcanization accelerator. *Elastomers* 92:165013u (1980).

SUMMARY OF THE INVENTION

The present invention resides In the discovery that DBH is inhibited by substituted 2-carboxyalkylthio 1-aralkylimidazoles, and the $C_{1-4}$alkyl ester derivatives thereof. These compounds are potent long acting DBH inhibitors.

The presently preferred compound of the invention and the compound included in the pharmaceutical compositions and used in the methods of the invention is 2-(carboxymethylthio)-1-(3,5-difluorobenzyl)imidazole.

The invention also is a method of inhibiting DBH activity in mammals, including humans, which comprises administering internally to a subject an effective amount of a substituted 2-carboxyalkythio-1-aralkylimidazole, or a $C_{1-4}$alkyl ester derivative thereof.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

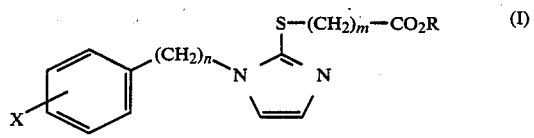

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;

n is 0–5;

m is 1–5;

R is H or $C_{1-4}$alkyl; or any pharmaceutically acceptable salt or hydrate thereof.

As used herein, "accessible combination thereof" means any combination of the substituents on the phenyl moiety that is available by chemical synthesis and is stable. $C_{1-4}$alkyl means a straight or branched chain alkyl having from 1 to 4 carbons.

Formula (I) compounds are prepared from corresponding phenylalkyl2-mercaptoimidazoles by processes such as shown in Scheme I, below. The starting phenylalkyl-2-mercaptoimidazoles are prepared from corresponding benzaldehydes or phenylalkylaldehydes by known processes such as shown in Scheme II, below, and described in European Patent Specification No. 125,033, published Nov. 14, 1984. In Scheme I, m and n are as described in Formula (I), $X^1$ is X as in Formula (I) except OH, and Z is bromo, chloro, fluoro, or iodo.

SCHEME I

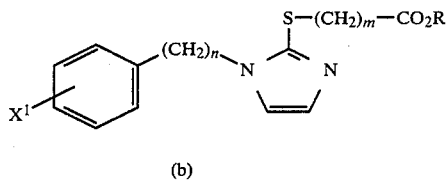

According to Scheme I, when a compound (b), a Formula (I) compound in which R is H, is the desired end product, a compound (a) and a haloalkanoic acid, preferably, chloro, are added to a mixture of a suitable solvent, preferably dimethyl formamide and water, and two molar equivalents of a base such as triethylamine, sodium hydroxide, potassium carbonate, or, preferably, potassium hydroxide to yield a compound (b), as illustrated in Example 1.

When Formula (I) compounds in which R is $C_{1-4}$alkyl are desired the haloalkyl acid, above, is replaced by a haloalkanoate ester such as in Example 9, below. The S-alkylation conditions employed are similar to those used for the carboxylic acids, with the exception that a single molar equivalent of strong base is required. These product carboxylate esters obviously may also serve as intermediates for the carboxylic acids themselves by subjecting the esters to mild hydrolytic conditions using either aqueous acid, for example aqueous hydrochloric acid or, preferably, aqueous base, for example aqueous sodium hydroxide. In the latter case, the final product is obtained by neutralizing the hydrolisate with aqueous acid, as in Example 10.

Formula (I) compounds in which X is OH are prepared from a compound (b) in which $X^1$ is $C_{1-4}$ alkoxy using known hydrolysis methods, for example by treatment with boron tribromide or hydrogen bromide in an appropriate solvent as exemplified in Example 2.

The phenylalkyl-2-mercaptoimidazoles used as starting materials in Scheme I are prepared from corresponding benzaldehydes or phenylalkylaldehydes using known processes such as shown in Scheme II below. The starting benzaldehydes and phenylalkylaldehydes are known and can be synthesized according to published procedures or can be obtained readily from various commercial suppliers. In Scheme II, $X^1$ is X as in Formula (I) except OH, n' is 1–5, and q is 0–4.

SCHEME II

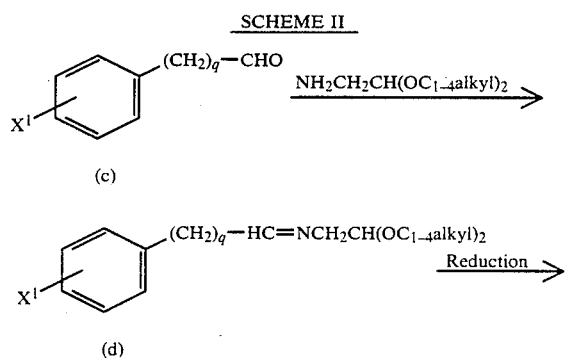

-continued
SCHEME II

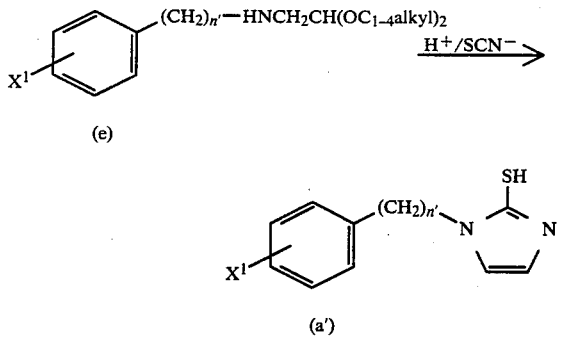

According to Scheme II, a compound (c) in a suitable organic solvent is reacted with an aminoacetaldehyde $diC_{1-4}alkylacetal$ to yield a compound (d). Thereafter, catalytic hydrogenation of a compound (d) using a suitable catalyst, preferably palladium on carbon, or reduction of a compound (d) using a suitable reducing agent such as sodium borohydride, lithium aluminum hydride, or aluminum hydride yields a compound (e). Reaction of a compound (e) with an acidic solution of a thiocyanate salt, preferably potassium thiocyanate in hydrochloric acid, yields a compound (a') which is a Scheme I compound (a) in which n is 1–5.

Formula (I) compounds in which n is 0 are synthesized from corresponding phenylimidazoles which are prepared by known processes such as reaction of an appropriately substituted phenyl isothiocyanate with an aminoacetaldehyde $diCl_{1-4}alkylacetal$ followed by strong acid catalyzed cyclization, as illustrated in Example 8, below.

Pharmaceutically acceptable acid addition salts of compounds of Formula I in which R is $C_{1-4}alkyl$ are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Pharmaceutically acceptable base addition salts of compounds of Formula I in which R is H are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine.

Because the Formula (I) compounds inhibit DBH activity, they are useful as diuretic, natriuretic, cardiotonic, antihypertensive, and vasodilator agents, as well as antiulcerogenic and anti-Parkinsonian agents.

Listed in Table I are Formula (I) compounds that were tested for in vitro DBH inhibition by a standard procedure for assaying conversion of tyramine to octopamine in the presence of DBH. J. J. Pisano, et al., *Biochim. Biophys. Acta*, 43, 566–568 (1960). Octopamine was assayed following sodium periodate oxidation to p-hydroxybenzaldehyde by measuring spectrophotometric absorbance at 330 nm. Inhibition is given in molar concentration of compound at which DBH activity was halved ($IC_{50}$). Fusaric acid, by this test, has an $IC_{50}$ of $8 \times 10^{-7}$ M; 2-(carboxymethylthio)-1-(3,5-difluorobenzyl)imidazole has an $IC_{50}$ of $4.2 \times 10^{-2}$ m.

Spontaneously hypertensive rats were treated with 2-(carboxymethylthio)-1-(3,5-difluorobenzyl)imidazole at a dose of 50 mg/kg intraperitoneally, and mean arterial blood pressure was monitored for four hours using an indwelling cannula in the femoral artery. When compared to vehicle treated controls, the animals treated with this compound exhibited significant blood pressure reductions within 30 minutes following treatment and remained significantly reduced for 4 hours. The maximal blood pressure reduction was approximately 43 mmHg.

Formula (I) compounds are incorporated into convenient pharmaceutical dosage forms such as capsules, tablets, or liquids for ingestion, injection, or inhalation. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any material used to give prolonged release of the active compound, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.1–100 mg/kg of active compound, preferably 0.1–50 mg/kg. The selected dose is administered to a human patient in need of DBH inhibition from 1–6 times daily, orally, rectally, by injection, by inhalation, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting DBH activity in mammals, including humans, comprises administering internally to a subject an effective DBH inhibiting amount of a Formula (I) compound.

The method of this invention of reducing blood pressure in mammals, including humans, comprises administering internally to a subject an effective amount of a Formula (I) compound.

The following examples are illustrative of preparation of Formula (I) compounds. The examples are not intended to limit the scope of the invention as defined hereinabove and as claimed below.

EXAMPLE 1

2-(Carboxymethylthio)-1-(3,5-difluorobenzyl)imidazole 1-(3,5-Difluorobenzyl)-2-mercaptoimidazole (2.26 g, 0.010 mole) and chloroacetic acid (0.95 g, 0.010 mole) were dissolved in a mixture of dimethylformamide (10 ml) and water (0.5 ml), and potassium hydroxide (1.12 g, 0.020 mole) in water (10 ml) was added dropwise with stirring at ambient temperature over 30 minutes. Stirring at ambient temperature was continued for five hours. The solution was then diluted with water (10 ml) and acidified with concentrated hydrochloric acid. A trace of precipitate formed. The mixture was filtered and the pH of the filtrate was adjusted to 5.5 with concentrated ammonium hydroxide and the mixture was extracted with three portions of methylene chloride. Concentration of the combined extracts gave a clear, heavy oil which was triturated with boiling ether. A white crystalline solid formed which was filtered and recrystallized from ethyl acetate hexane to give 1.18 g (42% yield) of 2-(carboxymethylthio)-1-(3,5-difluorobenzyl)imidazole, mp 101°–103° C.

EXAMPLE 2

2-(Carboxymethylthio)-1-(4-hydroxybenzyl)imidazole

The Example 1 process wherein 1-(3,4-difluorobenzyl)-2-mercaptoimidazole is replaced by (4-methoxybenzyl)-2-mercaptoimidazole yields 2-(carboxymethylthio)-1-(4-methoxybenzyl)imidazole. Treatment of this compound in methylene chloride with boron tribromide yields 2-(carboxymethylthio)-1-(4-hydroxybenzyl)imidazole.

EXAMPLE 3

2-(Carboxymethylthio)-1-(phenylbutyl)imidazole

The Example 1 procedure wherein 1-(3,5-difluorobenzyl)-2-mercaptoimidazole is replaced by 1-(1-phenylbutyl)-2-mercaptoimidazole yields 22-(carboxymethylthio)-1-(1-phenylbutyl)imidazole.

EXAMPLE 4

2-(Carboxymethylthio)-1-(3,5-difluoro-4-methoxybenzyl)imidazole

The Example 1 process wherein 1-(3,5-difluorobenzyl)-2-mercaptoimidazole is replaced by 1-(3,5-difluoro-4-methoxybenzyl)-2-mercaptoimidazole yields 2-(carboxymethylthio)-1-(3,5-difluoro 4-methoxybenzyl)imidazole.

EXAMPLE 5

2-(Carboxymethylthio)-1-(2,4,6-trichloro-3-methoxy-5-trifluoromethylbenzyl)imidazole The Example 1 procedure wherein 1-(3,5-difluorobenzyl)-2-mercaptoimidazole is replaced by 1-(2,4,5 trichloro-3-methoxy-5-trifluoromethylbenzyl)-2-mercaptoimidazole yields 2-(carboxymethylthio)-1-(2,4,5-trichloro-3-methoxy-5-trifluoromethylbenzyl)imidazole.

EXAMPLE 6

2-(Carboxymethylthio)-1-(4-cyanobenzyl)imidazole

The Example 1 process wherein 1-(3,5-difluorobenzyl)-2-mercaptoimidazole is replaced by 1-(4-cyanobenzyl)-2-mercaptoimidazole yields 2-(carboxymethylthio)-1-(4-cyanobenzyl)imidazole.

EXAMPLE 7

2-(Carboxymethylthio)-1-(4-nitrobenzyl)imidazole

The Example 1 process wherein 1-(3,5-difluorobenzyl)-2-mercaptoimidazole is replaced by 1-(4-nitrobenzyl)-2-mercaptoimidazole yields 2-(carboxymethylthio)-1-(4-nitrobenzyl)imidazole.

EXAMPLE 8

2-(Carboxymethylthio)-1-(4-methoxyphenyl)imidazole

A solution of 10 g (0.06 mole) of p-methoxyphenyl isothiocyanate in 100 ml of chloroform was treated with 6.3 g (0.06 mole) of aminoacetaldehyde dimethyl acetal. The solvent was evaporated and the residue was recrystallized from ethanol to yield N-(p-methoxyphenyl)-N'-($\beta,\beta$-dimethoxyethyl)thiourea, 9.2 g (57%). A suspension of this thiourea in a solution of 5 ml of concentrated sulfuric acid and 20 ml of water was refluxed for 3 hours. The mixture was cooled and a solid was filtered, washed with water, and dried. Recrystallization from ethanol gave 1-(4-methoxyphenyl)-2-mercaptoimidazole, 4.9 g (70%), mp 215°–217° C.

The Example 1 procedure wherein 1-(3,5-difluorobenzyl)-2-mercaptoimidazole is replaced by 1-(4-methoxyphenyl)-2-mercaptoimidazole yields 2-(carboxymethylthio)-1-(4-methoxyphenyl)imidazole.

EXAMPLE 9

2-(2-Carbomethoxyethylthio)-1-(3,5-difluorobenzyl)imidazole 1-(3,5-Difluorobenzyl)-2-mercaptoimidazole (2.26 g, 0.010 mole) and potassium hydroxide (0.56 g, 0.010 mole) in dimethylformamide (10 ml) containing water (0.5 ml) are stirred under argon at ambient temperature and methyl-3-bromo propionate (1.67 g, 0.010 mole) is added in one portion. The reaction mixture is heated at 95° C. for sixteen hours, cooled and extracted three times with ether. The combined ether extracts are concentrated to give an oil. This is purified by flash chromatography on silica gel eluting with methanol in methylene chloride to give 2-(2-carbomethoxyethylthio)-1-(3,5-difluorobenzyl)imidazole.

EXAMPLE 10

2-(2-Carboxyethylthio)-1-(3,5-difluorobenzyl)imidazole 2-(2-Carbomethoxyethylthio)-1-(3,5-difluorobenzyl)imidazole (3.12, 0.010 mole) is stirred with 2.5N aqueous sodium hydroxide (20 ml) and the reaction mixture is heated at reflux for one hour and then cooled and neutralized with concentrated hydrochloric acid. The mixture is then extracted three times with ether and the combine ether extracts are concentrated. A crystalline solid is obtained by trituration of the residue with boiling hexane. This is recrystallized from ethyl acetate-hexane to give 2-(2-carboxyethylthio)-1-(3,5-difluorobenzyl)imidazole.

EXAMPLE 11

An oral dosage form for administering the presently invented compounds is produced by screening, mixing, and filling into hard gelatin capsules the ingredients in the proportions shown in Table I, below.

TABLE I

| Ingredients | Amounts |
| --- | --- |
| 2-(Carboxymethylthio)-1-(3,5- | 50 mg |

TABLE I-continued

| Ingredients | Amounts |
| --- | --- |
| difluorobenzyl)imidazole | |
| magnesium stearate | 5 mg |
| lactose | 75 mg |

Example 12

The sucrose, calcium sulfate dihydrate, and Formula (I) compound shown in Table II below, are mixed and granulated in the proportions shown with a 10% gelatin solution. The wet granules are screened, dried, mixed with the starch, talc and stearic acid, screened, and compressed into a tablet.

TABLE II

| Ingredients | Amounts |
| --- | --- |
| 2-(Carboxymethylthio)-1-(3,5-difluorobenzyl)imidazole | 100 mg |
| calcium sulfate dihydrate | 150 mg |
| sucrose | 20 mg |
| starch | 10 mg |
| talc | 5 mg |
| stearic acid | 3 mg |

Example 13

2-(Carboxymethylthio)-1-(3,5-difluorobenzyl)imidazole dihydrochloride, 75 mg, is dispursed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites at a sufficient rate and in sufficient amounts to produce physiologic activity of Formula (I) compounds. Such compounds also would be included in the invented pharmaceutical compositions and used in the invented methods.

While the preferred embodiments of the invention are illustrated by the above, it is to be understood that the invention is not limited to the precise instructions herein disclosed and that the right to all modifications coming within the scope of the following claims is reserved.

We claim:

1. A method of inhibiting dopamine-$\beta$-hydroxylase activity in mammals that comprises administering an effective amount of a compound of the formula:

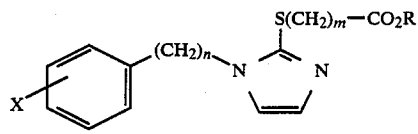

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2Cf_3$, or $CO_2C_aH_{2A+1}$ wherein a is 1-5, or any accessible combination thereof of up to 5 substituents;

n is 0-5;

m is 1-5;

R is H or $C_{1-4}$alkyl; or a pharmaceutically acceptable salt or hydrate thereof.

2. A method of claim 1 wherein n is 1.

3. A method of claim 2 wherein m is 1.

4. A method of claim 3 wherein R is H.

5. A method of claim 4 wherein the compound is 2-(carboxymethylthio)-1-(3,5-difluorobenzyl)imidazole.

6. A method of reducing blood pressure in mammals that comprises administering an effective amount of a compound as defined in claim 1.

* * * * *